US00PP36510P2

(12) United States Plant Patent
Michael

(10) Patent No.: US PP36,510 P2
(45) Date of Patent: Feb. 25, 2025

(54) ***XSEMPONIUM* PLANT NAMED 'Vortex'**

(50) Latin Name: ***XSemponium* spp.**
Varietal Denomination: Vortex

(71) Applicant: Surreal Succulents, Marazion (GB)

(72) Inventor: Daniel Michael, Marazion (GB)

(73) Assignee: SURREAL SUCCULENTS, Cornwall (GB)

( * ) Notice: Subject to any disclaimer, the term of this patent is extended or adjusted under 35 U.S.C. 154(b) by 0 days.

(21) Appl. No.: 18/631,218

(22) Filed: Apr. 10, 2024

(30) Foreign Application Priority Data

Dec. 4, 2023 (QZ) ..... PBR 20232641

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Zachariah Allan Kay
(74) *Attorney, Agent, or Firm* — Penny J. Aguirre

(57) ABSTRACT

A new cultivar of X*Semponium* plant named 'Vortex' that is characterized by its compact and low growth habit, its foliage that is thick and sturdy with glossy surfaces, its large, strong rosettes (up to 50 cm across) with many leaf layers down the stem giving it a vortex-like spiral form, and its unique foliage coloration that is dark purple-red with green centers.

2 Drawing Sheets

Botanical classification: X*Semponium* spp.
Variety denomination: 'Vortex'.

CROSS-REFERENCE TO RELATED APPLICATIONS

This application claims priority to European Community Plant Variety Office (CPVO) Plant Breeder's Rights Application No. 2023/2641 filed on Dec. 4, 2023, under 35 U.S.C. 119(f), the entire contents of which is incorporated by reference herein. The Applicant received the information for the Plant breeders' rights application directly from the Inventor.

BACKGROUND OF THE INVENTION

The present invention relates to a new and distinct cultivar of X*Semponium* spp., an intergeneric hybrid, and referred to hereinafter by its cultivar name, 'Vortex'. The new cultivar of X*Semponium* is a frost hardy succulent subshrub perennial grown for ornamental foliage use in landscapes and containers.

The new cultivar arose from an ongoing breeding program by the Inventor in Penzance, Cornwall, United Kingdom. The goal of the breeding program was to produce new cultivars of X*Semponium* with unique foliage coloration, compact growth habits, low growing, dense and neat plant habits, and large rosettes.

The new cultivar arose from a cross made by the Inventor in 2015 between *Sempervivum ciliosum* 'Green Ice' (not patented) as the female parent and Aeonium 'Ice Warrior' (not patented) as the male parent. The Inventor selected 'Vortex' as a single unique plant amongst the seedlings that resulted from the above cross in 2016.

Asexual propagation of the new cultivar was first accomplished by the Inventor by stem root cuttings in 2016 in Penzance, Cornwall, United Kingdom. Asexual propagation by stem root cuttings and offshoots has determined the characteristics to be stable and reproduced true to type in successive generations.

SUMMARY OF THE INVENTION

The following traits have been repeatedly observed and are determined to be the characteristics of the new cultivar. These attributes in combination distinguish 'Vortex' as a unique cultivar of x *Semponium*.

1. 'Vortex' exhibits a compact and low growth habit.
2. 'Vortex' exhibits foliage that is thick and sturdy with glossy surfaces.
3. 'Vortex' exhibits large, strong rosettes (up to 50 cm across) with many leaf layers down the stem giving it a vortex-like spiral form.
4. 'Vortex' exhibits unique foliage coloration that is dark purple-red with green centers.

The female parent plant differs from 'Vortex' in having foliage that is green in color with no red margins, a smaller plant size with smaller rosettes, a less robust growth habit and a flatter plant habit. The male parent plant differs from 'Vortex' in having longer stems, fewer leaves per rosette, a plant habit that is less dense, leaves that are broader in size with less pointed tips, foliage that is green with margins that are dusty purple in color and inflorescences that are less robust, less firm, and more open in stature. 'Vortex' can be most closely compared to the X*Semponium* cultivars 'Destiny' (U.S. Plant Pat. No. 35,495) and 'Diamond' (U.S. Plant Pat. No. 35,564). Both 'Destiny' and 'Diamond' are similar to 'Vortex' in having a low growing habit and large sized rosettes. 'Destiny' differs from 'Vortex' in having leaves that are larger in size, foliage that is darker purple in color, and a less spiraled and less dense growth pattern with leaves that are less upward facing. 'Diamond' differs from 'Vortex' in having a less spiraled growth pattern, foliage that is less upward facing and green in color with red margins, and slightly smaller leaves.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Monrovia, Jordan's Jungle, Surreal Succulents, National Gardening Association, YouTube, Manoj Malde Garden Design, R.H.S., Listen Notes, Greenhouse Product News, Hortweek, Plantipp, Cascadian Nurseries, Gerbeaud, Instagram, Gartenpraxis, IPM Essen, matteoragni, Bloeman, Au Cactus Francophone, Cactusmania, Reddit, Lawn & Garden Retailer, Mr. Plant Geek, Captivate fm, Apple, and Suttons.

BRIEF DESCRIPTION OF THE DRAWINGS

The accompanying color photographs illustrate the overall appearance and distinct characteristics of the new cultivar.

The photograph in FIG. 1 was taken of a plant 1 year in age as grown in a greenhouse in a 17-cm container in Waddinxveen, The Netherlands.

Figure 1:
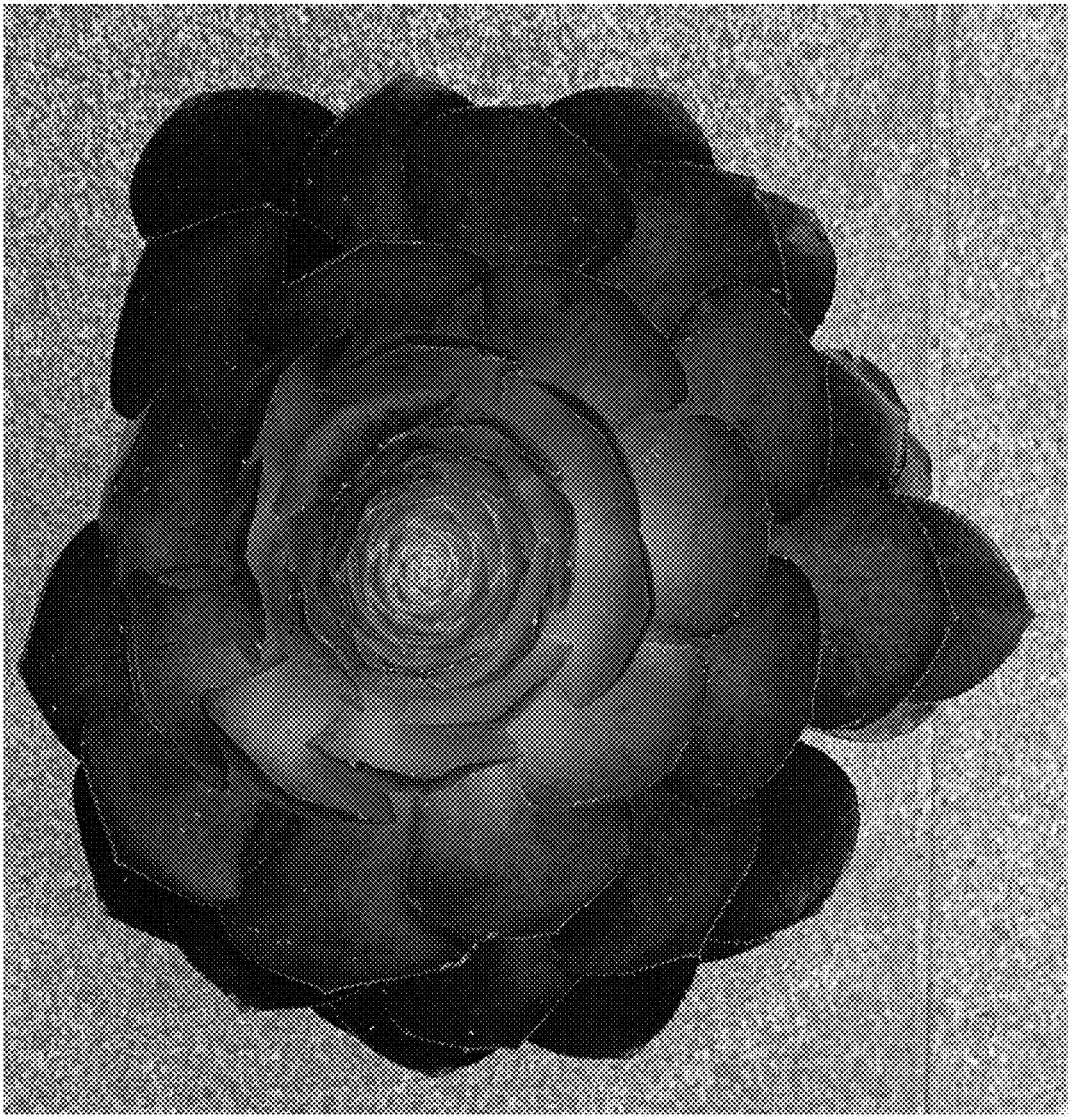
FIG. 1 provides a top view of a rosette of 'Vortex'.
Figure 2:
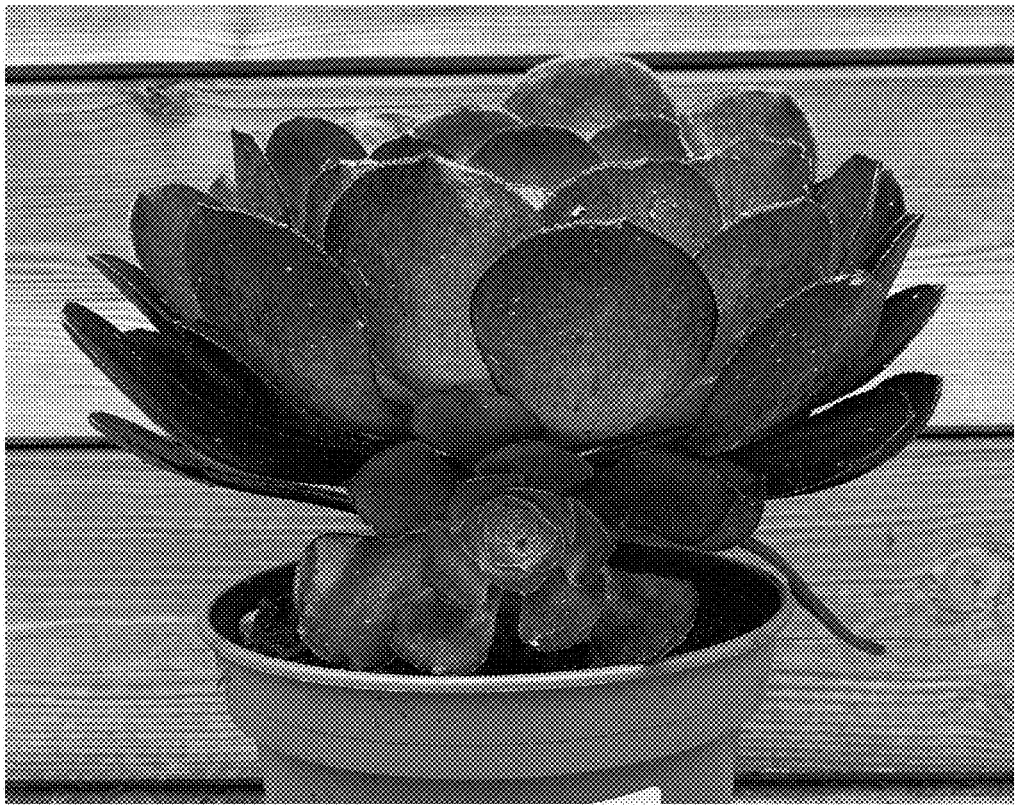

The photograph in FIG. 2 provides a side view of a rosette of 'Vortex'.

Figure 3:
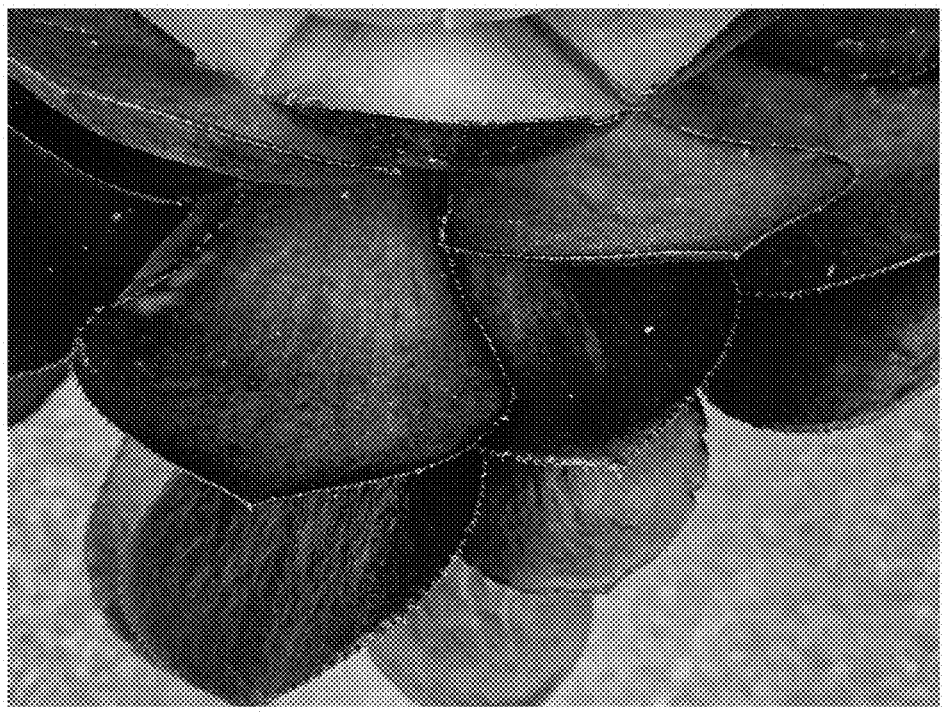

The photograph in FIG. 3 provides a close-up view of the leaves of 'Vortex'.

The colors in the photographs may differ slightly from the color values cited in the detailed botanical description, which accurately describe the colors of the new X*Semponium*.

DETAILED BOTANICAL DESCRIPTION

The following is a detailed description of the new cultivar as observed on 1-year-old plants of 'Vortex' as grown in a greenhouse in 17-cm containers in Waddinxveen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen succulent perennial.

*Plant shape*.—Conical.

*Plant habit*.—Compact, low growing, dense basal rosette arranged in a dense spiral form with offsets clustered around main rosette.

*Height and spread*.—Reaches 15 cm in height and 24 cm in diameter as a one-year-old plant growing in a container.

*Hardiness*.—At least hardy to −5° C., has not been tested in colder climates.

*Diseases and pests*.—No susceptibility or resistance to diseases or pests has been observed.

*Root description*.—Fibrous.

*Propagation*.—Root stem cuttings and offsets.

*Root development*.—Roots initiate in 6 to 8 weeks and fully root as a young plant in a P7 container in about 2 months.

*Growth rate*.—Moderate.

Stem description:

*Stem shape*.—Cylindrical.

*Stem size*.—1.9 cm in width and up to 2.5 cm in length.

*Stem surface*.—Smooth with leaf scars.

*Stem arrangement*.—Only 1 main stem.

*Stem aspect*.—80° from horizontal.

*Internode length*.—Not applicable.

*Stem color*.—145A, scars 199B.

Foliage description:

*Leaf shape*.—Spathulate.

*Leaf division*.—Simple.

*Leaf arrangement*.—Rosette.

*Leaf quantity*.—Average of 100 per rosette.

*Leaf base*.—Narrowly cuneate.

*Leaf apex*.—Round, mucronate.

*Leaf venation*.—No veins visible.

*Leaf margins*.—Ciliate.

*Leaf attachment*.—Sessile.

*Leaf orientation*.—Flat to slightly concave and held upward.

*Leaf substance*.—Succulent, thick and sturdy.

*Leaf surface*.—Both surfaces smooth and glossy.

*Leaf color*.—Young; upper and lower surface; 144B, margins 183A, mature; upper surface a blend of 144B, 183A and 187A, base 144D, lower surface 144A, top and margins 187A.

*Leaf size*.—Average of 11 cm in length and 4.8 cm in width (top), 1.4 cm in width (base).

*Rosette size*.—Average of 24 cm in diameter and 15 cm in height (can reach up to 50 cm in diameter with age), offsets an average of 7 cm in height and 10.5 cm in width.

Flower description: No flowers produced to date.

It is claimed:

1. A new and distinct variety of X*Semponium* plant named 'Vortex' as described and illustrated herein.

* * * * *